United States Patent
Williams

(10) Patent No.: US 11,412,996 B2
(45) Date of Patent: Aug. 16, 2022

(54) MULTI-ZONE BED PAD HAVING HIGH-SPEED DETECTION OF BED EXIT

(71) Applicant: Rondish Company Limited, Kwai Chung (HK)

(72) Inventor: Steven Alfred Williams, Kwai Chung (HK)

(73) Assignee: Rondish Company Limited, Kwai Chung (HK)

( * ) Notice: Subject to any disclaimer, the term of this patent is extended or adjusted under 35 U.S.C. 154(b) by 0 days.

(21) Appl. No.: 17/272,775

(22) PCT Filed: Sep. 11, 2019

(86) PCT No.: PCT/IB2019/057666
§ 371 (c)(1),
(2) Date: Mar. 2, 2021

(87) PCT Pub. No.: WO2020/053788
PCT Pub. Date: Mar. 19, 2020

(65) Prior Publication Data
US 2021/0315528 A1    Oct. 14, 2021

Related U.S. Application Data

(60) Provisional application No. 62/730,640, filed on Sep. 13, 2018.

(51) Int. Cl.
*A61B 5/00* (2006.01)
*G08B 21/04* (2006.01)
*G08B 29/18* (2006.01)
*A61B 5/11* (2006.01)

(52) U.S. Cl.
CPC ............ *A61B 5/746* (2013.01); *A61B 5/6892* (2013.01); *G08B 21/0461* (2013.01); *G08B 29/185* (2013.01); *A61B 5/1115* (2013.01); *A61B 2562/046* (2013.01)

(58) Field of Classification Search
CPC combination set(s) only.
See application file for complete search history.

(56) References Cited

U.S. PATENT DOCUMENTS

| 5,844,488 A | 12/1998 | Musick |
| 2008/0169931 A1 | 7/2008 | Gentry et al. |
| 2014/0125486 A1 | 5/2014 | Williams |
| 2015/0035671 A1 | 2/2015 | Williams |

FOREIGN PATENT DOCUMENTS

GB    2464965 A    5/2010

*Primary Examiner* — Nabil H Syed
*Assistant Examiner* — Cal J Eustaquio
(74) *Attorney, Agent, or Firm* — Mintz Levin Cohn Ferris Glovsky and Popeo, P.C.

(57) ABSTRACT

A sensor pad (105) is adapted to be positioned under or atop a mattress of a patients bed (205) as part of a monitoring system that provides a signal to a caregiver when the patient (305) rises from the bed (205). The pad (105) defines a total area, and wherein the total area is divided into a plurality of zones (Z1, Z2, Z3, Z4, Z5). A timing of issuance of an alarm triggered by the pad (105) varies based upon which zone (Z1, Z2, Z3, Z4, Z5) of the pad (105) a patient (305) is detected to be located upon.

6 Claims, 6 Drawing Sheets

MULTI-ZONE BED PAD HAVING HIGH-SPEED DETECTION OF BED EXIT

CROSS-REFERENCES TO RELATED APPLICATIONS

This application is a National Stage entry, filed under 35 U.S.C. § 371, of International Application No. PCT/M2019/057666, filed on Sep. 11, 2019, and claims priority to U.S. Provisional Application No. 62/730,640, filed on Sep. 13, 2018, entitled "MULTI-ZONE BED PAD WITH HIGH SPEED DETECTION OF BED EXIT", the contents of which are herein incorporated by reference in their entirety.

BACKGROUND

The use of bed detection pads and alarm units as part of a fall management solution for patient care is well established though-out the world. However, a common drawback is that patient movement on the pad can cause false alarms, such as to a nursing unit monitoring the patient, which can result in alarm fatigue. This means that a nurse can tend to ignore alarms over time after getting used to a large quantity of false alarms.

In addition, the actual exit alarm may occur too late to provide the nurse with sufficient time to react to the patient's exit from the bed. This is because the patient must vacate the bed before the alarm sounds. As a result, the alarm may sound or otherwise activate after a fall off the bed by the patient.

In view of the foregoing, there is a need for improved bed pads with alarm capabilities.

SUMMARY

Disclosed is a bed a sensor or detection pad that has a predetermined delay in alarm activation such as while the patient is in a predetermined, first location of the bed. For example, the alarm may have a delayed activation while the patient is positioned in a middle location of the bed. The alarm may also have a relatively fast reaction and alarm activation when it is detected that the patient is in a second location of the bed, such as on or near the edge of the bed. In a nonlimiting example, the second location is a location of the bed where the patient is likely to be exiting the bed, such as the edge of the bed.

The bed pad is configured to detect a patient leaving a bed prior to when the patient actually leaves the bed. This may be accomplished, for example, by providing a bed detection pad that has different zones that correspond to different locations on the bed. The bed detection pad may delay issuance of an alarm or provide a timing parameter for an alarm based upon what zone on the bed was triggered by the presence of the patient.

In one aspect, there is disclosed a bed monitoring pad, comprising: a planar pad coupled to electrical circuitry configured to detect a location of a patient atop the pad, wherein the pad is configured to trigger the issuance of an alarm based upon a patient's location relative to the pad, and wherein the pad defines a total area, and wherein the total area is divided into a plurality of zones, and wherein a timing of issuance of an alarm triggered by the pad varies based upon which zone of the pad a patient is detected to be located upon.

The details of one or more variations of the subject matter described herein are set forth in the accompanying drawings and the description below. Other features and advantages of the subject matter described herein will be apparent from the description and drawings, and from the claims.

DETAILED DESCRIPTION

Before the present subject matter is further described, it is to be understood that this subject matter described herein is not limited to particular embodiments described, as such may of course vary. It is also to be understood that the terminology used herein is for the purpose of describing particular embodiments only, and is not intended to be limiting. Unless defined otherwise, all technical terms used herein have the same meaning as commonly understood by one skilled in the art to which this subject matter belongs.

A standard bed detection pad is typically made of two printed plates (such as plastic plates) that contact one another when pressed, such as when a patient is positioned on the pad to exert sufficient force to press the plates against one another. The plates contact one another or otherwise coupled with one another through a flexible material such as sponge positioned between the plates when a patient is positioned on top of the pad. The pad may also use paper or cloth materials for this purpose and/or fits on top or under a mattress of the bed. The pad essentially detects when the patient's weight is removed from the pad, which weight removal releases the plates from contact with one another to thereby electrically trigger issuance of an alarm, such as an audio alarm or a visual alarm, or both.

The removal of the patient's weight from the pad and decoupling of the pads from one another causes an open circuit and a trigger of an alarm. The bed pad includes only one circuit on each side of the bed. Thus, the bed pad treats a weight removal equally over the whole area of the pad.

Disclosed is a bed pad system that separates the pad into different zones across a bed or other resting surface such as over an area defined by the pads. For example, the area defined by the pad may have a first zone on the first location of the area, a second zone on the second, separate location of the area, and so on. The different zones correspond to different reaction times for triggering an alarm.

Figure 1:
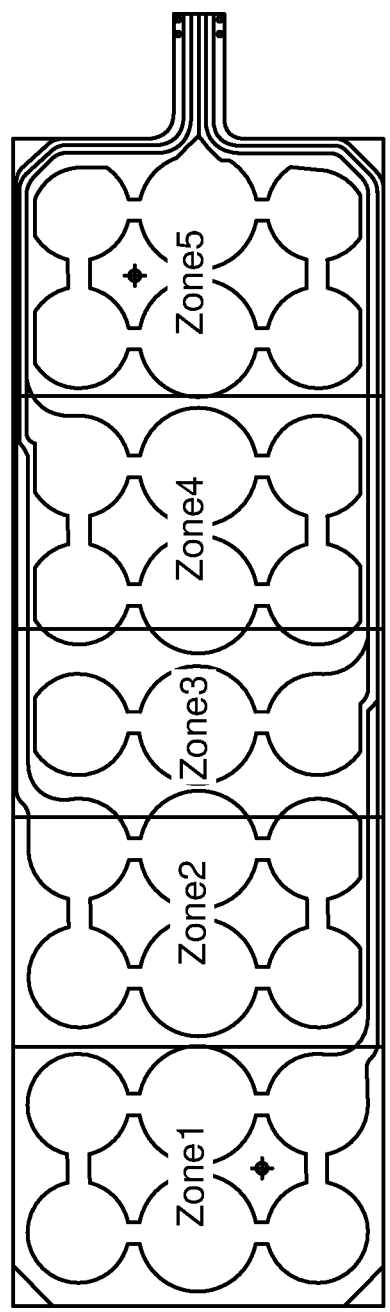
FIG. 1 shows a schematic representation of a bed pad.

FIG. 1 shows a representation of a bed pad 105 having five zones distributed among an area defined by the bed pad 105. The bed 105 pad can be a planar element, such as a pillow or pad and can have upper and lower surfaces that define an area. In an actual embodiment, the bed pad 105 can be covered with a material, such as PVC, that covers or otherwise protects the internal contents of the bed pad. For example, the bed pad 105 can have a variety of electrical circuits that can detect one a patient is lying on the bed pad. The bed pad can be positioned atop a patient's mattress or below patient's mattress such that it is positioned to detect when the patient is positioned atop the mattress.

In some implementations, a bed monitoring pad is provided that includes a first flexible plate with conductive material and a second plate with conductive material in which the first flexible plate includes at least two zones of conductivity.

In a related aspect, some implementations describe a patient monitoring system that includes an alarm indicator and a bed monitoring pad that includes a first flexible plate with conductive material and a second plate with conductive material in which the first flexible plate includes at least two zones of conductivity.

In the example shown in FIG. 1, the bed pad 105 has five zones including zone 1, zone 2, zone 3, zone 4, and zone 5. In this example, the bed pad has a length with zones 1 through zone 5 being distributed consecutively along the length of the bed pad 105. It should be appreciated however that the location, size, and shape of the zones can vary and can be distributed among various locations with various sizes and shapes along the area of the bed pad 105. The zones can each define a completely non-integrated area or can overlap with one another or can be arranged such that the zones do not overlap with one another.

Figure 2:
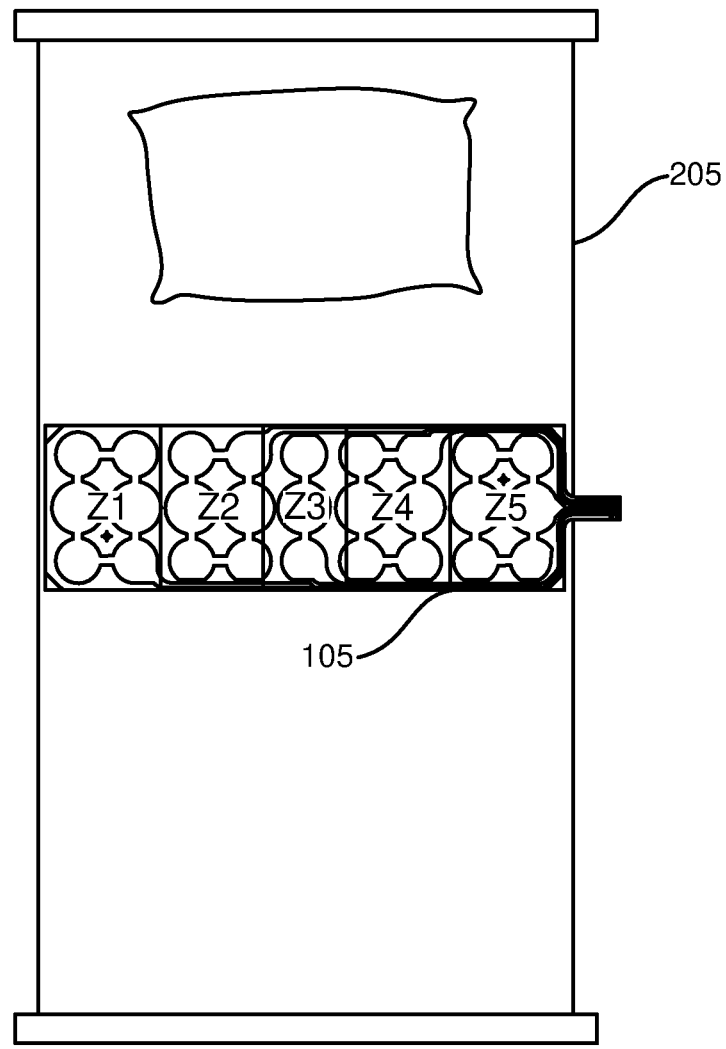
FIG. 2 shows a schematic representation of the bed pad position atop a bed.

In the example of FIG. 1, the zones are positioned in a manner such that the zones can be spatially distributed across the width of a bed. FIG. 2 shows a top, schematic view of a bed 205. In the example of FIG. 2, the pad 105 is positioned on the bed 205 such that the zones are distributed across the width of the bed 205 with zone 1 (Z1) being located at or near a first side edge of the bed 205 and zone 5 (Z5) being located at or near a second, opposite side edge of the bed. In this situation, zone 1 and zone 5 are external zones and that they are positioned at external edges of the pad. The pad can also include internal zones that are positioned within internal locations of the pad and separated from an external edge of the pad by the external zones. The zones 2 (Z2), zone 3 (Z3), and zone 4 (Z4) are distributed consecutively in between zone 1 and zone 5 such that a plurality of zones cover or are distributed along the entire width of the bed 205. In the illustrated example, the pad includes five zones although this number may vary. As mentioned, the size, shape, and spatial distribution of the zones may also vary.

Figure 3:
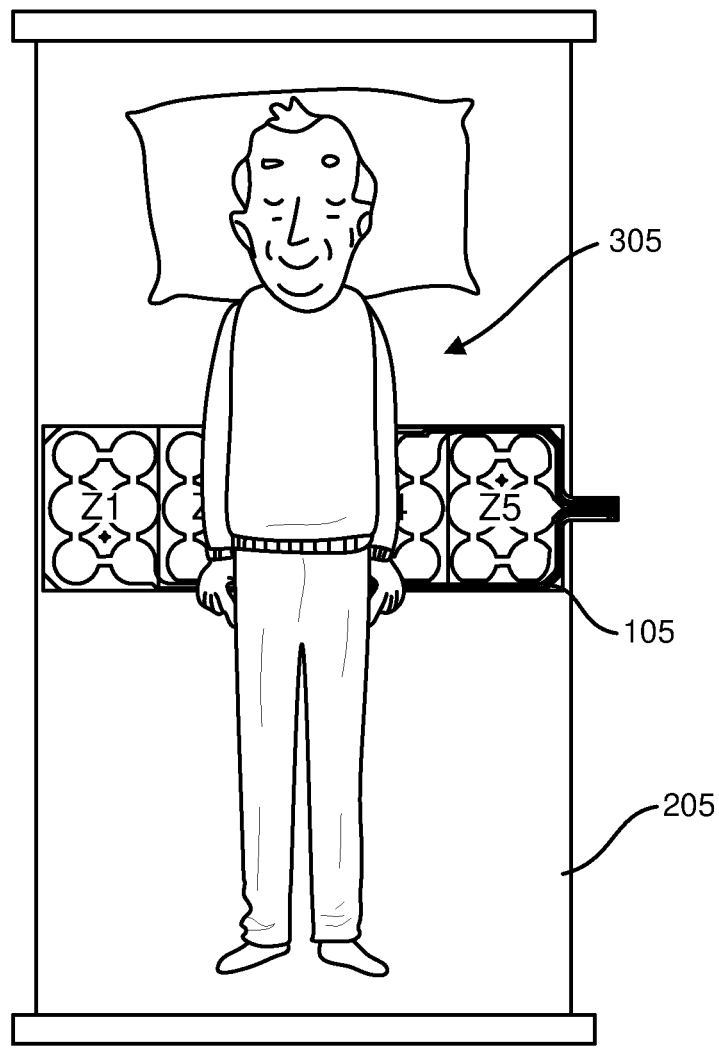
FIG. 3 shows a schematic representation of a patient position on the bed pad with the patient being positioned at a central location of the bed.
Figure 4:
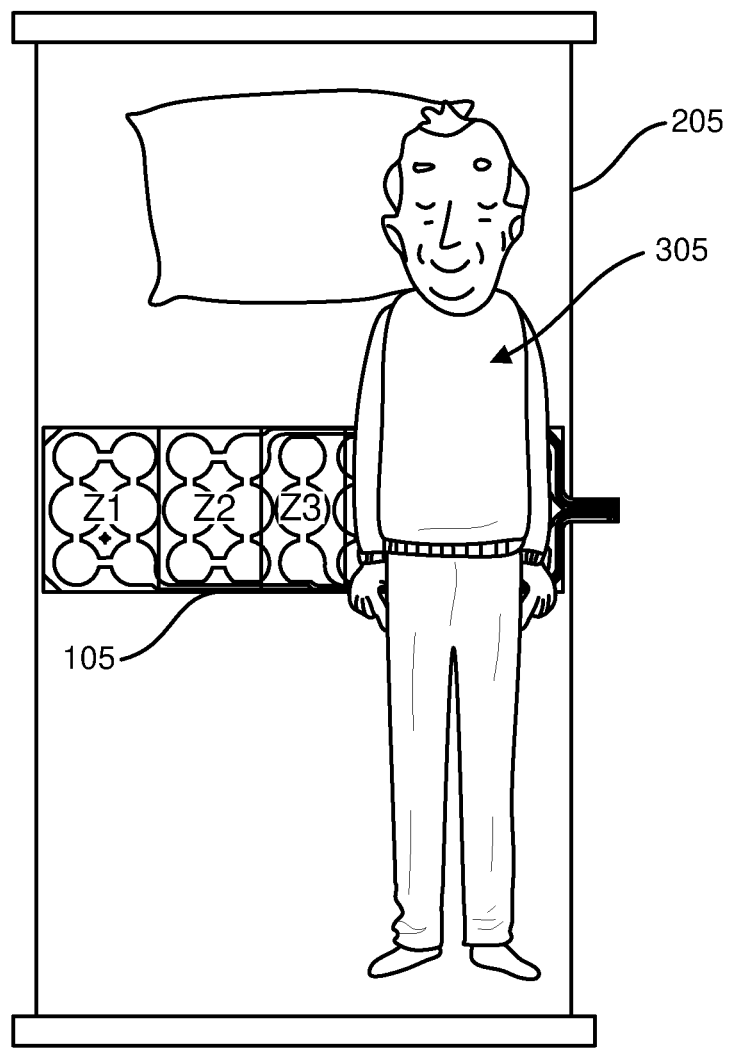
FIG. 4 shows a schematic representation of the patient positioned on the bed pad near an edge of the bed.

This configuration permits the various zones of the pad 105 to detect current location and/or movement of the patient over the width of the bed. FIG. 3 shows a schematic representation of a patient atop the bed 205. In the example of FIG. 3, the patient is located along a central position in the bed 205 such as for example the patient being located atop zones 2, 3, 4, or atop only a single zone based upon the relative size of the patient and zone. This configuration permits the pad 105 to detect movement from side-to-side across the bed. That is, as the patient moves along the width of the bed, the patient will be positioned upon or otherwise contact different zones which will detect and identify the location along the width of the bed where the patient is located. FIG. 4 shows the patient located at or near a side edge of the bed such that the patient is positioned atop, for example, zones 4 and 5. This configuration can also provide data related to where the patient is positioned on the bed regardless of whether or not the patient is moving or is going to be.

This configuration can be used to detect when the patient moves to the edge of the bed. The pattern 105 can include or otherwise be coupled to software as well as a computer processor that can particularly assign different sensitivity (such as delays in issuing an alarm) based on the position of the patient on the bed. This can be done, for example, using over and under mattress pads.

For example, if the patient is in a central location on the bed (as shown in FIG. 3), there is likely little risk that the patient will imminently leave the bed given that the patient is at a central location of the bed. But any patient movement and or self-lifting above the pad can trigger an alarm, which may very well be a false trigger given that the patient is located in the bed center and may not imminently leave the bed. This is particularly a problem if it triggers a wireless signal for a cordless version or causes an alarm on a nurse-call system. However, there may be no risk or little risk of immediate patient exit from the bed.

Therefore, in the situation where the patient is located on the center of the bed (as shown in FIG. 3), a longer delay in alarm triggering is desirable, such as, for example, a delay of 3-4 second. Such a delayed alarm would correspond to zones 3 and 4 of the bed pad being occupied by the patient. The longer delay is relative to the amount of time that it takes to trigger an alarm when patient location on one of the other zones is detected. For example, the bed pad can a trigger an alarm after a five second delay the patient is detected to be located in the middle zone of the bed, all the bed pad can trigger an alarm after a smaller delay or even trigger an immediate alarm if the patient is detected to be located on an outer zone of the bed such as near the edge of the bed.

If the patient is laying or otherwise positioned near the edge on the bed, such as shown in FIG. 4, there is a greater risk of patient bed exit although not necessarily imminent. In this case a shorter delay from triggering an alarm can occur, such as on the order of 1-2 seconds. This corresponds to both the edge (i.e. zones 1 or 5) and one central zone (i.e. zones 2 or 4) of the bed pad being occupied by the patient.

Figure 5:
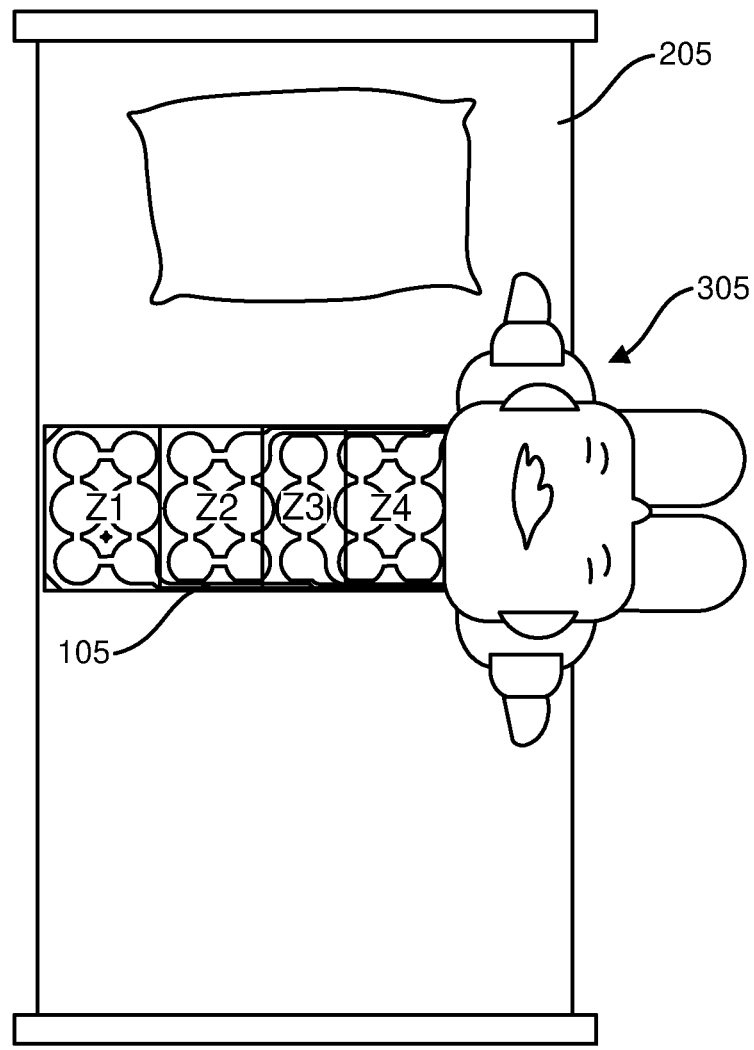
FIG. 5 shows a schematic representation of the patient positioned in a seating position on an edge of the bed.
Figure 6:
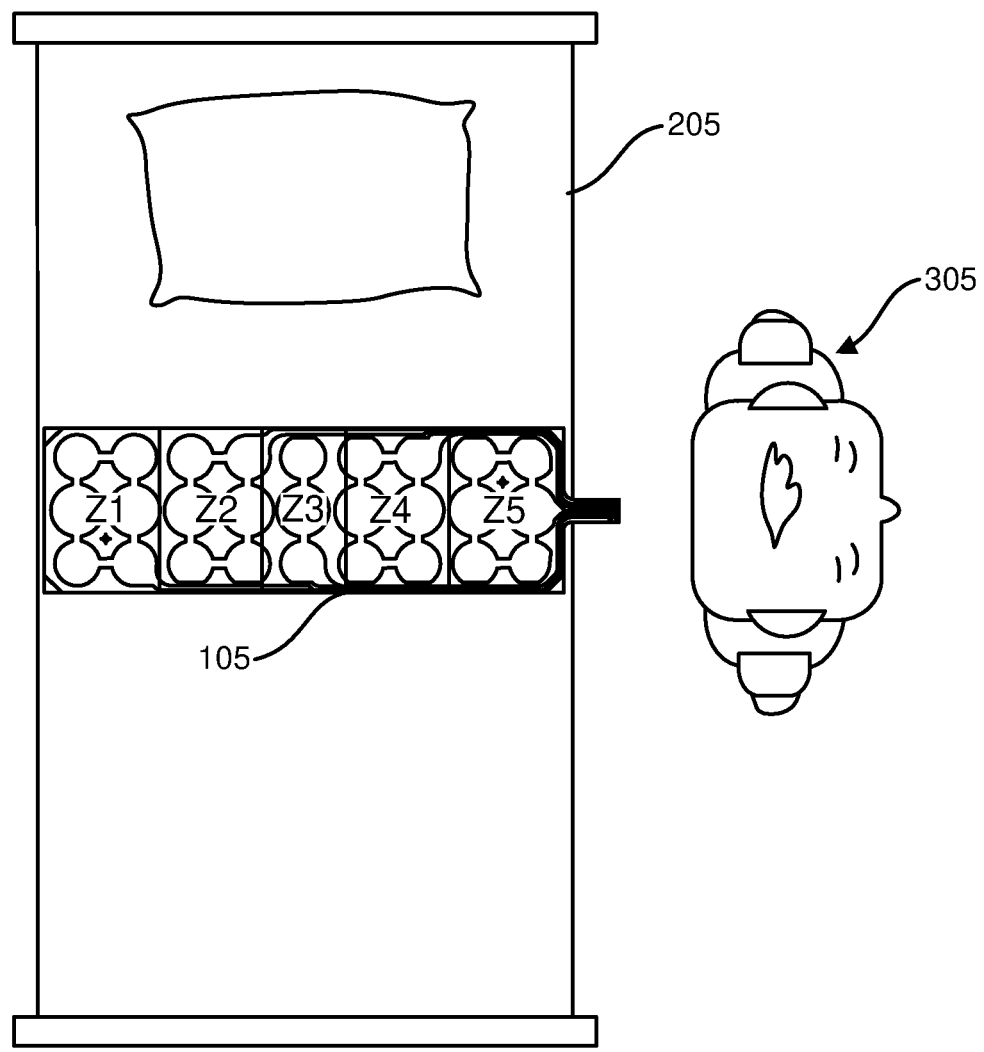
FIG. 6 shows a schematic representation of the patient positioned off the bed.

FIG. 5 shows an example where the patient 305 is positioned (i.e., in a sitting position) near an edge of the bed, which can correspond to the patient being positioned atop zone 5. If the patient moves to sit on the edge of the bed (as shown in FIG. 5) this can be deemed high risk and imminent exit of the patient from the bed. In this case, if the patient sits for a short time (such as about 2 seconds) then an alarm is immediately triggered. Or, if the patient then leaves the pad (such as shown in FIG. 6 with a patient has exited the bed) after only the edge zone was occupied for any amount of time then an alarm is immediately triggered. This corresponds to a patient moving quickly to the edge of the bed. In such a case, no delay occurs to trigger instant alarm.

In a method of use, there is provided a bed pad that the texts whether a patient is located atop the pad. The bed had triggers an alarm if it is detected that the patient's body has moved away from a particular location on the path. The bed pad can be configured with different zones with each his own corresponding to a particular area of the pad. The timing for issuance of an alarm can vary based upon the location of the pad where it is detected that the patient is located or ceased to be located.

Another drawback of current systems that occurs under hospital acquired injuries is bed sores, which is the number one problem developed while in the hospital (falls are number two). The disclosed system may be used to provide a profile of the movement of the patient by detecting the different zones and then send a signal to a central point to analyze and determine if action is required such as turning the patient.

Another application of this multi-zoned pad is to detect if a baby turns and therefore moves onto a different zone. This is important to make sure the baby does not turn onto his/her face and thereby cause breathing problems. In this case, a smaller version is used and placed in cot or just under the baby on the bed under the baby's bed sheets. It can also detect if the baby leaves the bed or area which also may be of concern.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A bed monitoring pad, comprising:
a planar pad coupled to electrical circuitry configured to detect a location of a patient atop the pad, wherein the pad is configured to trigger the issuance of an alarm based upon a patient's location relative to the pad, and wherein the pad defines a total area, and wherein the total area is divided into a plurality of zones, and wherein a timing of issuance of an alarm triggered by the pad varies based upon which zone of the pad a patient is detected to be located upon;
and wherein the pad is divided into at least five zones including a first external zone and a second external zone, each external zone being positioned along an outer edge of the pad, and wherein the pad further includes at least a first internal zone, a second internal zone, and a third internal zone, wherein each of the first internal zone, the second internal zone, and the third internal zone is positioned between the first external zone and the second external zone;
wherein a timing of issuance of an alarm has a longer delay for at least one of the first internal zone, the second internal zone and the third internal zone of the pad relative to a timing of issuance of an alarm for either the first external zone or the second internal zone of the pad.

2. A bed monitoring pad, comprising:
a planar pad coupled to electrical circuitry configured to detect a location of a patient atop the pad, wherein the pad is configured to trigger the issuance of an alarm based upon a patient's location relative to the pad, and wherein the pad defines a total area, and wherein the total area is divided into a plurality of zones, and wherein a timing of issuance of an alarm triggered by the pad varies based upon which zone of the pad a patient is detected to be located upon;
and wherein the pad is divided into at least five zones including a first external zone and a second external zone, each external zone being positioned along an outer edge of the pad, and wherein the pad further includes at least a first internal zone, a second internal zone, and a third internal zone, wherein each of the first internal zone, the second internal zone, and the third internal zone is positioned between the first external zone and the second external zone;
wherein a timing of issuance of an alarm has a longer delay for at least one of the first internal zone, the second internal zone and the third internal zone of the pad relative to a timing of issuance of an alarm for either the first external zone external zone or the second internal zone of the pad.

3. The bed monitoring pad of claim 1, wherein at least one internal zone is separated from an outer edge of the pad by the at least one external zone.

4. The bed monitoring pad of claim 1, wherein the pad is rectangular.

5. The bed monitoring pad of claim 1, wherein at least one of the first internal zone, the second internal zone, and the third internal zone overlaps with another of the first internal zone, the second internal zone, and the third internal zone.

6. The bed monitoring pad of claim 5, wherein the third internal zone is positioned between to the first internal zone and the second internal zone and wherein the third internal zone overlaps with at least the first internal zone and the second internal zone.

* * * * *